(12) United States Patent
Wu

(10) Patent No.: US 8,206,327 B2
(45) Date of Patent: Jun. 26, 2012

(54) HEAD MASSAGER AND DISTANCE ADJUSTMENT DEVICE THEREOF

(75) Inventor: Xu Liang Wu, Shenzhen (CN)

(73) Assignee: Shenzhen Breeze Technology Co., Ltd., Shenzhen (CN)

( * ) Notice: Subject to any disclaimer, the term of this patent is extended or adjusted under 35 U.S.C. 154(b) by 199 days.

(21) Appl. No.: 12/092,269

(22) PCT Filed: Oct. 19, 2007

(86) PCT No.: PCT/CN2007/003003
§ 371 (c)(1),
(2), (4) Date: May 1, 2008

(87) PCT Pub. No.: WO2008/124978
PCT Pub. Date: Oct. 23, 2008

(65) Prior Publication Data
US 2010/0113991 A1    May 6, 2010

(30) Foreign Application Priority Data

Apr. 13, 2007    (CN) .......................... 2007 1 0074045

(51) Int. Cl.
*A61H 1/00*    (2006.01)
*A42B 1/22*    (2006.01)

(52) U.S. Cl. ........... 601/46; 2/171; 2/183; 2/410; 2/417; 602/17

(58) Field of Classification Search ...... 2/410, 417–420, 2/171, 183, DIG. 10, DIG. 11, 7, 8.1–8.8; 601/46, 84, 15, 48, 70, 71, 79, 148–152, 601/DIG. 15; 602/17; 24/68 R, 68 B
See application file for complete search history.

(56) References Cited

U.S. PATENT DOCUMENTS

| | | | | |
|---|---|---|---|---|
| 3,375,529 | A | * | 4/1968 | Timm et al. ........................ 2/8.1 |
| 5,421,799 | A | * | 6/1995 | Rabin et al. ...................... 601/71 |
| 7,707,695 | B2 | * | 5/2010 | Dubois .......................... 24/68 B |
| 2006/0200052 | A1 | * | 9/2006 | Lin ................................. 601/70 |
| 2006/0245175 | A1 | * | 11/2006 | Heine et al. .................... 362/105 |
| 2008/0184451 | A1 | * | 8/2008 | Lemke et al. ...................... 2/8.2 |

* cited by examiner

*Primary Examiner* — Patricia Bianco
*Assistant Examiner* — Keri J Nelson

(57) ABSTRACT

A head massager includes a helmet (10) having a first parallel hoop (11) and a second parallel hoop (12) connected to each other for forming a ring surrounding the user's head. The helmet (10) has a first meridian hoop (21) and a second meridian hoop (22) connected to each other to form an arc structure and hang the head massager on user's head. The distance adjustment devices (3) are provided to connect the first parallel hoop (11), the second parallel hoop (12), the first meridian hoop (21), and the second meridian hoop (22) together for adjusting the size of the helmet (10) to provide a comfortable fit to user's head.

1 Claim, 13 Drawing Sheets

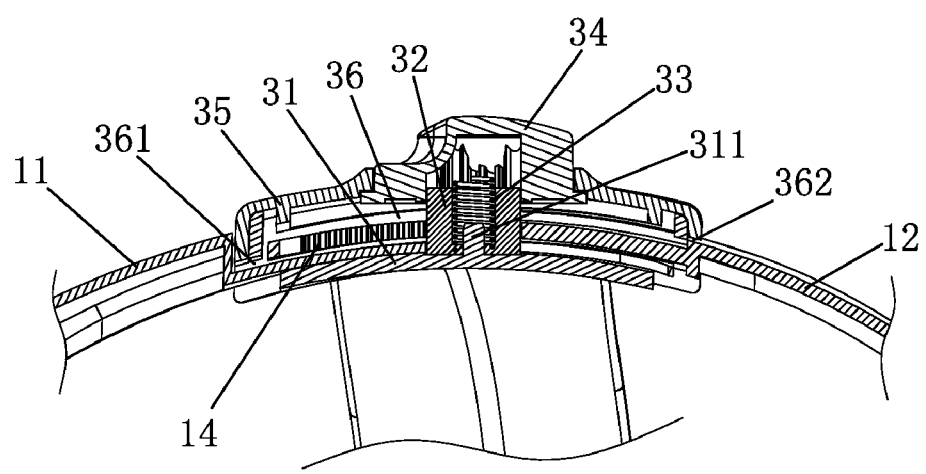
FIG. 5
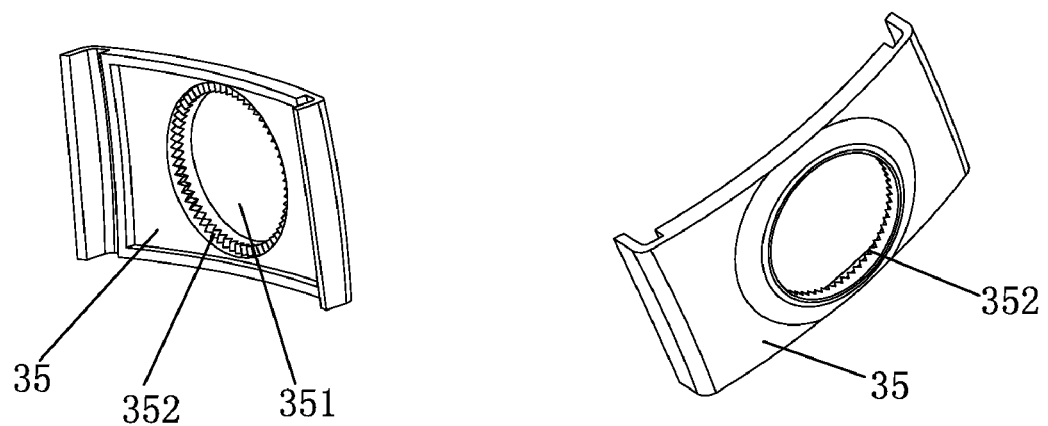
FIG. 6
FIG. 7

HEAD MASSAGER AND DISTANCE ADJUSTMENT DEVICE THEREOF

BACKGROUND OF THE INVENTION

1. Field of the Invention

The present invention relates to a head massager, and more particularly to a head massager having a distance adjustment device for adjusting a head perimeter of the head massager.

2. Description of Related Art

A conventional head massager in accordance with the prior art has a helmet for wearing on user's head and massaging the user's head via a massage device that in mounted in the helmet. However, the size of the helmet of the conventional head massager is unchangeable such that some user may feel the helmet is too big and some user may feel too small. Consequently, the helmet of the conventional head massager can not provide comfort to everyone who uses it. In addition, the conventional head massager has a complicated structure and a monotone massage way.

The present invention has arisen to mitigate and/or obviate the disadvantages of the conventional head massager.

SUMMARY OF THE INVENTION

The main objective of the present invention is to provide an improved head massager that has a plurality of distance adjustment devices for adjusting the size of the helmet to provide comfort to user's head.

To achieve the objective, the distance adjustment device in accordance with the present invention comprises a seat and a drive gear rotatably mounted on the seat and rotated along an axis thereof. A knob is slidably mounted to the drive gear. The knob is rotated and moved along an axis thereof. The knob includes a first gear ring and a second gear ring formed respectively thereon. The first gear ring is engaged with the drive gear. A cover is mounted to the seat and has a third gear ring formed therein. The third gear ring is engaged with the second gear ring of the knob. A reset elastic member is partially received in the drive gear along the axis of the knob. The reset elastic member abuts against the knob for providing a restitution force to the knob after the knob being inward pressed.

The seat has a stub extending therefrom and the drive gear has a through hole centrally and longitudinally defined therein for pivotally receiving the stub.

The through hole in the drive gear is a sunken hole and divided in to a first section and a second section, wherein the first section having a diameter smaller than that of the second section such that an annular plane is formed between the first section and the second section. The reset elastic member is received in the second section and sleeved on the stub for resetting the knob. The reset elastic member has two opposite ends respectively abutting against the annular plane and the knob.

The knob has an inner periphery and an outer periphery, wherein the first gear ring is formed on the inner periphery of the knob and the second gear ring is formed on the outer periphery of the knob. The cover has an opening defined therein and the third gear ring formed on an inner periphery of the opening.

The knob has a protrusion centrally extending therefrom and extending through the opening in the cover for user to easily rotate the knob.

The head massager in accordance with the present invention comprises a helmet having a first parallel hoop and a second parallel hoop connected to each other for forming a ring surrounding the user's head. The helmet has a first meridian hoop and a second meridian hoop connected to each other to form an arc structure and hang the head massager on user's head. Three distance adjustment devices are provided to connect the first parallel hoop, the second parallel hoop, the first meridian hoop and the second meridian hoop. Each distance adjustment device comprises a seat and a drive gear rotatably mounted on the seat and rotated along an axis thereof. A knob is slidably mounted to the drive gear. The knob is rotated and moved along an axis thereof. The knob includes a first gear and a second gear ring formed thereon, wherein the first gear ring is engaged with the drive gear. A cover is mounted to the seat and has a third gear ring formed therein. The third gear ring is engaged with the second gear ring of the knob. A reset elastic member is partially received in the drive gear along the axis of the knob. The reset elastic member abuts against the knob for providing a restitution force to the knob after the knob being inward pressed. Each of first parallel hoop and the second parallel hoop has a series of adjustment teeth formed on two opposite ends thereof and engaged with the drive gear of a corresponding of the distance adjustment device. Each of the first meridian hoop and the second meridian hoop has a first end connected to each other by a corresponding one of the distance adjustment devices and a second end secured on a corresponding on of the distance adjustment devices that connect the first parallel hoop and the second parallel hoop. The first end of each of the first meridian hoop and the second meridian hoop has a series of adjustment teeth formed thereon and engaged with the drive gear of the corresponding distance adjustment device that connects the first meridian hoop and the second meridian hoop.

Each of the first parallel hoop and the second parallel hoop has two opposite ends each having a parallel groove defined therein and the series of adjustment teeth of each of the two parallel hoops is formed on one side of a corresponding one of the parallel grooves. The first end of each of the first meridian hoop and the second meridian hoop has a meridian groove defined therein and the series of teeth of each of the two meridian hoops is formed on one side of a corresponding of meridian grooves.

The seat has a stub extending therefrom and the drive gear has a through hole centrally and longitudinally defined therein for pivotally receiving the stub. The through hole in the drive gear is a sunken hole and divided in to a first section and a second section, wherein the first section having a diameter smaller than that of the second section such that an annular plane is formed between the first section and the second section. The reset elastic member is received in the second section and sleeved on the stub for resetting the knob. The reset elastic member has two opposite ends respectively abutting against the annular plane and the knob.

The seat has a first slot and a second slot respectively defined in two opposite ends thereof to allow the first parallel hoop and the second parallel hoop extending into the distance adjustment device.

The knob has an inner periphery and an outer periphery, wherein the first gear ring is formed on the inner periphery of the knob and the second gear ring is formed on the outer periphery of the knob. The cover has an opening defined therein and the third gear ring is formed on an inner periphery of the opening.

The head massager further comprises massage pads, massage gasbags, and air pump, electric valves and a control device formed with control circuits. The air pump is electrically connected to the electric valves and the control circuits. Each of the parallel hoops and the meridian hoops includes an inner periphery having at least one massage pad mounted thereon and an edge of each of the massage pad is secured on an inner periphery of the helmet. Each massage pad has a chamber defined therein for receiving a corresponding one of the massage gasbags.

The head massager further comprises a plurality of heaters respectively secured to a surface of a corresponding one of the massage pads and electrically connected to the control circuit.

One of the massage pads has a trough defined therein for receiving a vibrator that has a vibrating block eccentrically mounted on a drive axle of the vibrator.

Each massage pad has a base and a pellet formed on the base. An edge of the base is secured on an inner periphery of the helmet and the base being flexible.

The control device includes a box separated from the helmet, and the air pump and the electric valves are received in the box.

Further benefits and advantages of the present invention will become apparent after a careful reading of the detailed description with appropriate reference to the accompanying drawings.

BRIEF DESCRIPTION OF THE DRAWINGS

FIG. 5 is a cross-sectional view of the head massager in FIG. 3 along line B-B;

FIG. 6 is a perspective view of a cover of the distance adjustment device in accordance with the present invention;

FIG. 7 is another perspective view of a cover of the distance adjustment device in accordance with the present invention;

DETAILED DESCRIPTION OF THE INVENTION

Figure 1:
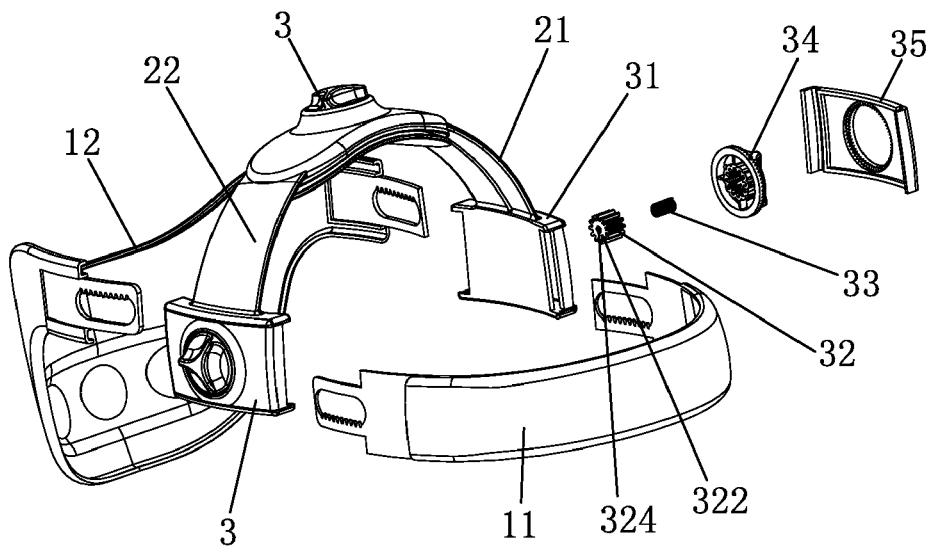
FIG. 1 is an exploded perspective view of a head massager with a distance adjustment device in accordance with the present invention.
Figure 2:
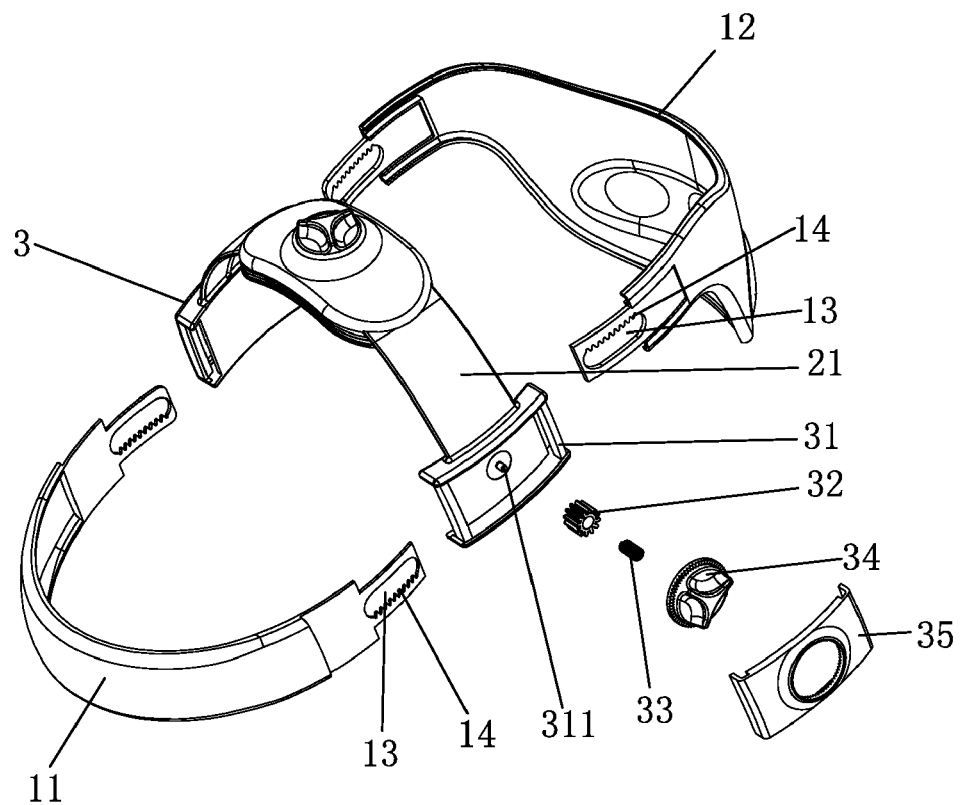
FIG. 2 is another exploded perspective view of the head massager with a distance adjustment device in accordance with the present invention.
Figure 3:
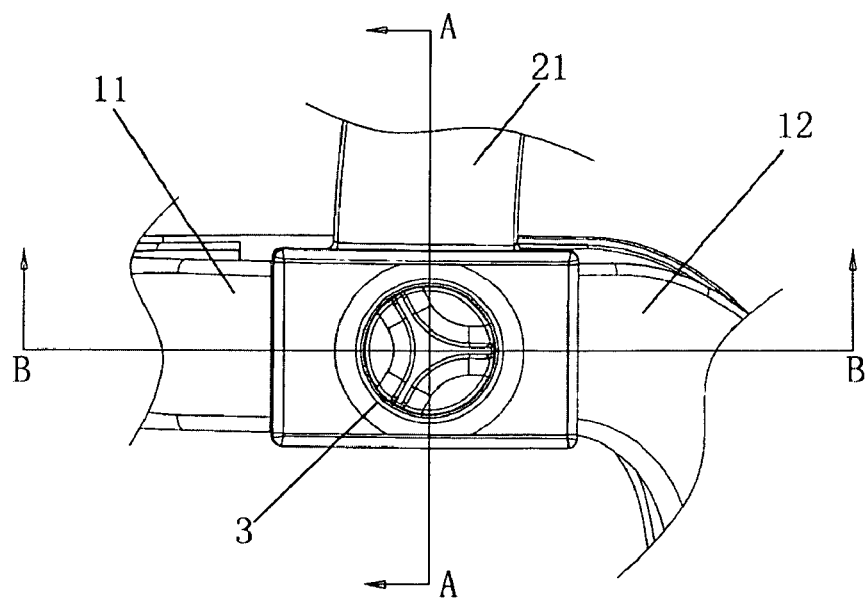
FIG. 3 is a partial side plan view of the head massager in accordance with the present invention.
Figure 4:
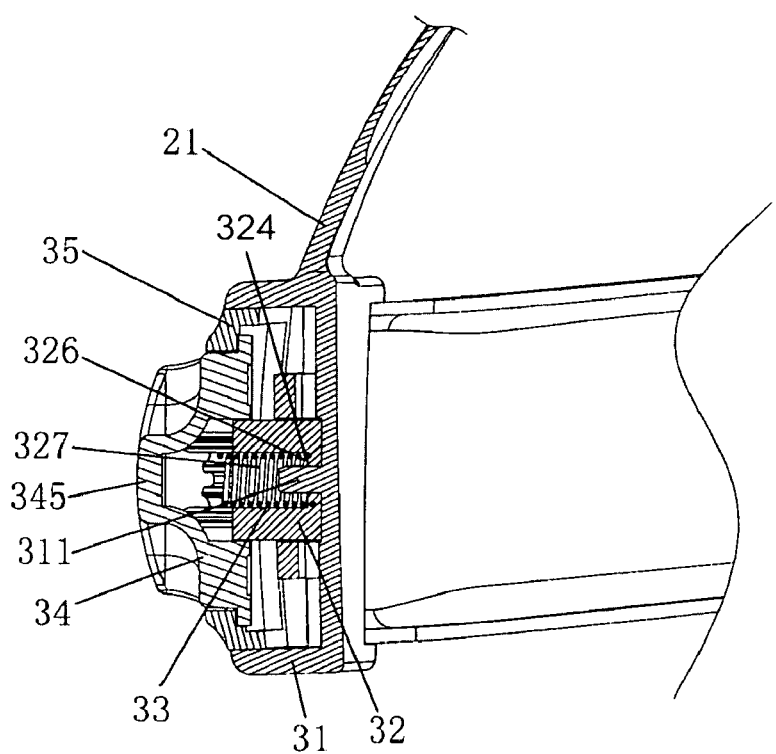
FIG. 4 is a cross-sectional view of the head massager in FIG. 3 along line A-A.
Figure 8:
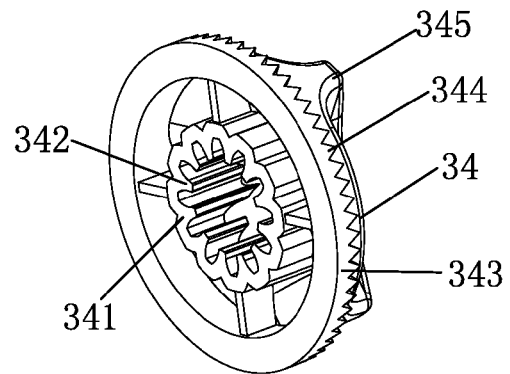
FIG. 8 is a perspective view of a knob of the distance adjustment device in accordance with the present invention.
Figure 9:
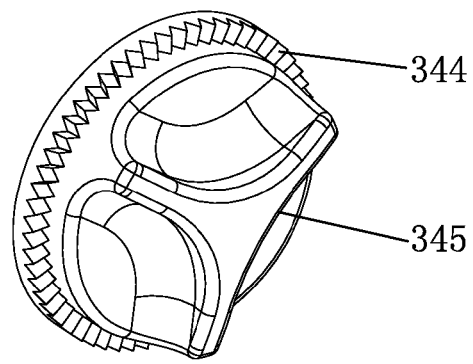
FIG. 9 is another perspective view of a knob of the distance adjustment device in accordance with the present invention.
Figure 10:
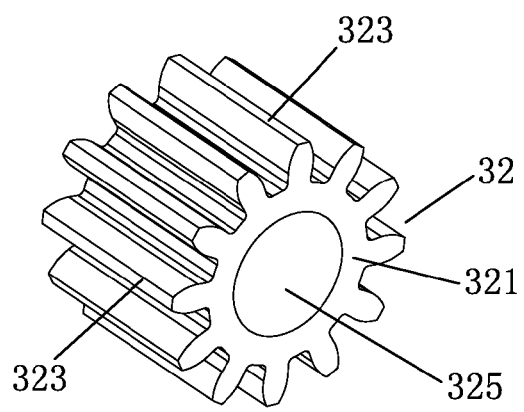
FIG. 10 is a perspective view of a drive gear of the distance adjustment device in accordance with the present invention.

Referring to the drawings and initially to FIGS. 1-10, a head massager in accordance with the present invention comprises a helmet (10) having a first parallel hoop (11) and a second parallel hoop (12) connected to each other for forming a ring surrounding the user's head. The helmet (10) has a first meridian hoop (21) and a second meridian hoop (22) connected to each other to form an arc structure and hang the head massager on user's head. The first meridian hoop (21) and the second meridian hoop (22) are made of tough plastic material such that the first meridian hoop (21) and the second meridian hoop (22) are flexible. Each of the first parallel hoop (11) and the second parallel (12) has two opposite ends each having a parallel groove (13) defined therein. One side of each of the parallel groove (13) has a series of adjustment teeth (14) formed thereon. Each of the first meridian hoop (21) and the second meridian hoop (22) has a first end connected to each other. A meridian groove is defined in the first end of each of the first meridian hoop (21) and the second meridian hoop (22). One side of each of the two meridian grooves has a series of adjustment teeth formed thereon.

There are three distance adjustment devices (3) are provided to connected the first parallel hoop (11), the second parallel hoop (12), the first meridian hoop (21) and the second meridian hoop (22). Two distance adjustment devices (3) are provided to connect the first parallel hoop (11) and the second parallel hoop (12) and the other one distance adjustment device (3) is provided to connected the first ends of each of the first meridian hoop (21) and the second meridian hoop (22). Each distance adjustment device (3) has a seat (31), a drive gear (32), a reset elastic member (33), a knob (34) and a cover (35). The seat (31) has a stub (311) centrally and laterally extending therefrom. The drive gear (32) is a spur gear and has a first side (321) and a second side (211). A ring of cogs (323) are radially and equally disposed on an outer periphery of the drive gear (32) between the first side (321) and the second side (322). A through hole (327) is centrally and longitudinally defined in the drive gear (32). The through hole (327) is a sunken hole. The through hole (327) is divided into a first section (324) and a second section (325), wherein the first section (324) has a diameter smaller than that of the second section (325) such that an annular plane (326) is formed between the first section (324) and the second section (325). The reset elastic member (33) is received in the second section (325) and sleeved on the stub (311) for resetting the knob (34). In the preferred embodiment of the present invention is a spring. The knob (34) includes an inner side (341) having a first gear ring (342) formed therein and an outer side (343) having a second gear ring (344) formed thereon. The knob (34) has a protrusion (345) centrally extending form the outer side (343) for user to easily operate the knob (34). The cover (35) has an opening (351) centrally defined therein and extending through the cover (35). A third gear ring (352) is formed on a periphery of the opening (351).

When assembling the distance adjustment device (3), the drive gear (32) is longitudinally mounted to the stub (311) and the stub (311) sequentially and longitudinally extends through the first section (324) and the second section (325) of the through hole (327) in the drive gear (32). The reset elastic member (33) is received in the second section (325) of the through hole (327) and sleeved on the stub (311). The knob (34) is mounted to the drive gear (32), wherein the drive gear (32) is partially received in the knob (34) and engaged with the first gear ring (341). The reset elastic member (33) has two opposite ends respectively abutting against the annular plane (326) and the inner side (341) of the knob (34). The cover (35) is securely mounted to the seat (31) for holding the drive gear (32) and the knob (34) in place, and forming a closed chamber (36) between the seat (31) and the cover (35). The second gear ring (344) of the knob (34) is engaged with the third gear ring (352) of the cover (35) and the protrusion (345) extends through the cover (35) via the opening (351) in the cover (35). The seat (31) has a first slot (361) and a second slot (362) respectively defined in two opposite ends thereof to allow the first parallel hoop (11) and the second parallel hoop (12) extending into the distance adjustment device (3).

As regards to the helmet (10) of the present invention, each of the first parallel hoop (11) and the second parallel hoop (12) has one end extending into a corresponding one of the three distance adjustment device (3) via the first slot (361) and the second slot (362). The drive gear (32) in the corresponding distance adjustment device (3) extends into the parallel groove (13) of each of the first parallel hoop (11) and the second parallel hoop (12) and engaged with the series of adjustment teeth (14) of each of the two parallel grooves (13). The series of adjustment teeth (14) of the first parallel hoop (11) and the series of adjustment teeth (14) of the second parallel hoop (12) face each other such that the first parallel hoop (11) and the second parallel hoop (12) are moved relative to each other when the drive gear (32) is rotated. A free end of each of the first meridian hoop (21) and the second meridian hoop (22) is respectively mounted to the two distance adjustment devices (3) that connects the first parallel hoop (11) and the second parallel hoop (12) to form a ring structure.

When adjusting the distance between the first parallel hoop (11) and the second parallel hoop (12), the knob (34) of the distance adjustment device (3), which connects the first parallel hoop (11) and the second parallel hoop (12), is inward pressed and the first gear ring (342) of the knob (34) is moved along the cogs (212) of the drive gear (32). The knob (34) is rotated relative to clock-wise/counter clock-wise for driving the dive gear (32) to move the first parallel hoop (11) and the second parallel hoop (12) due to the series of adjustment teeth (14) of each of the first parallel hoop (11) and the second parallel hoop (12) when the first gear ring (344) is disengaged from the third gear ring (352), and the reset elastic member (33) is compressed during the adjusting process. The knob (34) is released and moved to its original position due to the restitution force of the reset elastic member (33), and the second gear ring (344) of the knob (34) and the third gear ring (352) are engaged with each other again to lock the knob (34) when the first parallel hoop (11) and the second parallel hoop (12) are adjusted to a suitable position. The adjust way of the first meridian hoop (21) and the second meridian hoop (22) are the same as that of the first parallel hoop (11) and the second parallel hoop (12).

In the preferred embodiment of the present invention, the drive gear (32) is rotatably mounted on the bottom of the seat (31) and can be rotated relative to an axis thereof. The knob (34) can be rotated and moved along an axis thereof. The knob (34) can be rotated and moved along the axis thereof when being inward pressed and automatically moved to its original position along the axis thereof due to the restitution force of the reset elastic member (33) when being released. The knob (34) has a locked position and an adjusting position. In the locked position, the first gear ring (342) of the knob (34) is engaged with the cogs (323) of the drive gear (32) and the second gear ring (344) of the knob (34) is engaged with the third gear ring (352) of the cover (35). In the adjusting position, the first gear ring (342) of the knob (34) is engaged with the cogs (323) of the drive gear (32) and the second gear ring (344) of the knob (34) is disengaged from the third gear ring (352) of the cover (35).

In the preferred embodiment of the present invention, the axis of the drive gear (32) linearly corresponds to that of the knob (34). In addition, the first gear ring (342), the second gear ring (344) and the third gear ring (352) concentrically correspond to one another, and linearly align with the axis of each of the drive gear (32) and the knob (34). Certainly, the distance adjustment device (3) can be operated when the axis of the drive gear (32) is parallel to that of the knob (34).

Figure 11:
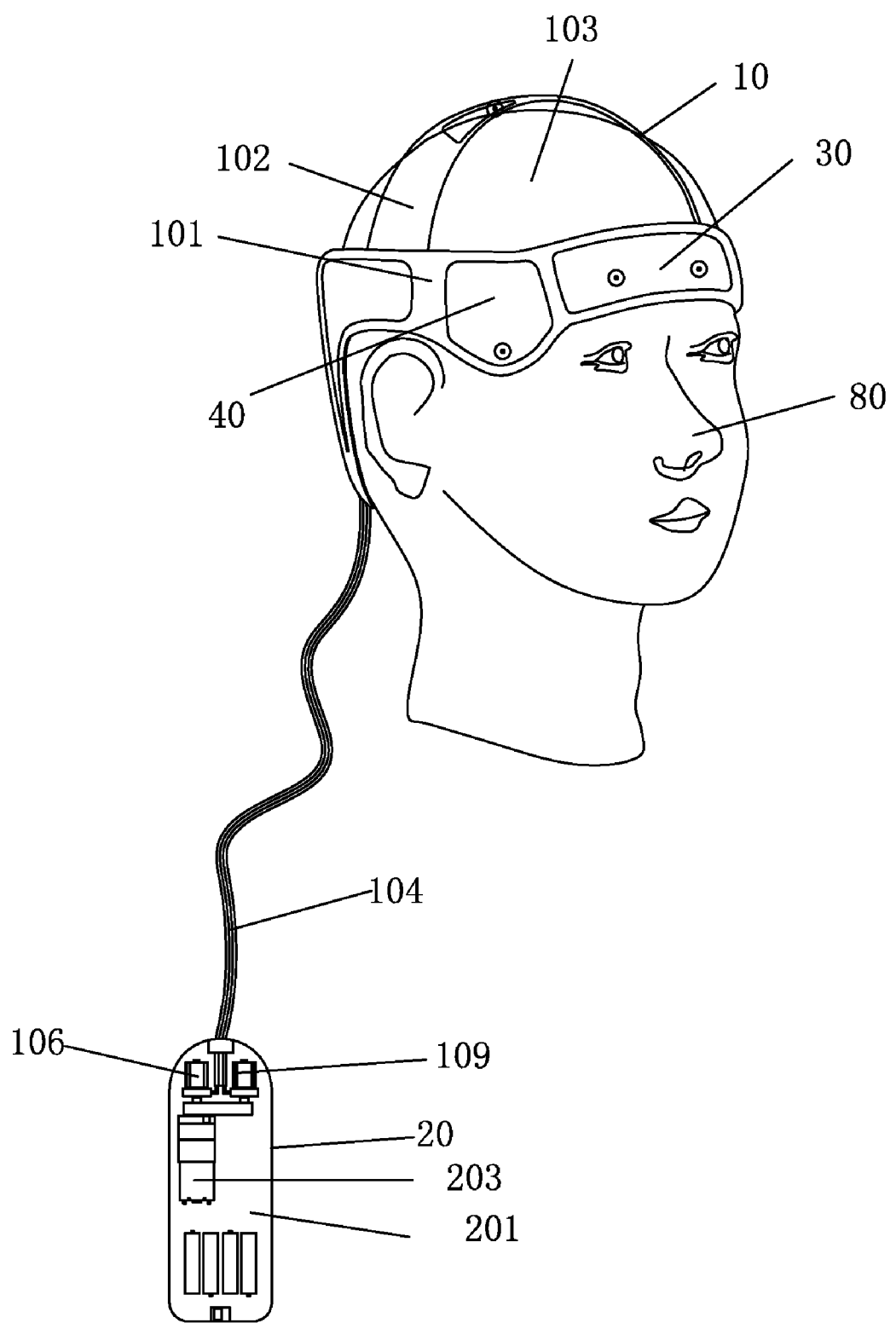
FIG. 11 is a schematic view of the head massager in accordance with the present invention.
Figure 12:
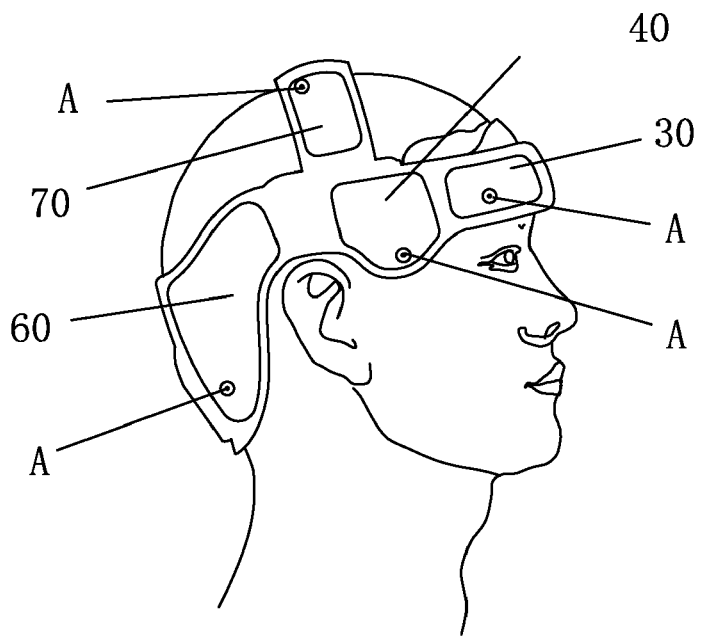
FIG. 12 is a side plan view of the head massager in accordance with the present invention for showing the side massage gasbag.
Figure 13:
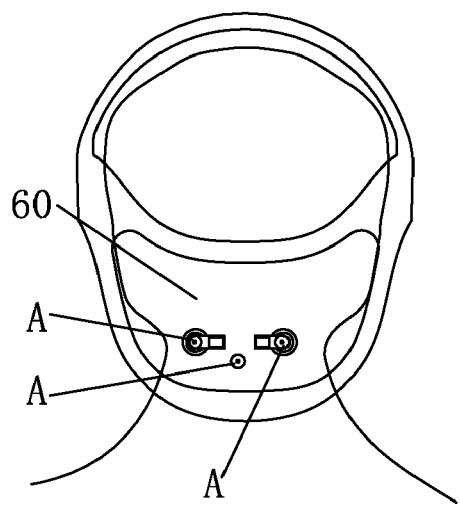
FIG. 13 is a rear plan view of the head massager in accordance with the present invention for showing the rear massage gasbag.
Figure 14:
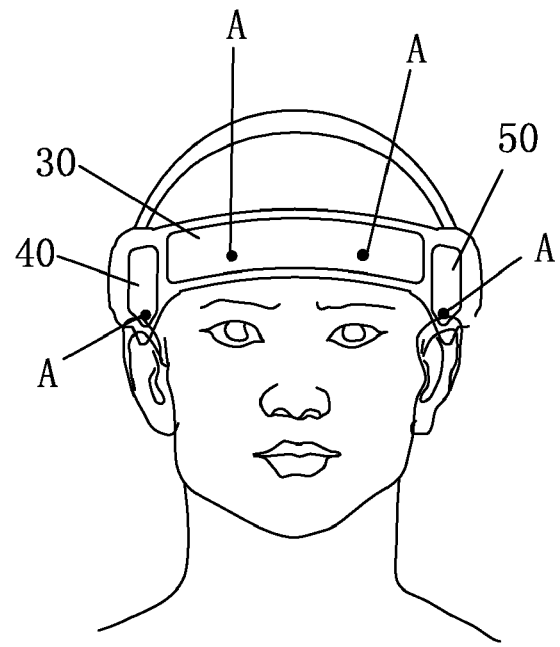
FIG. 14 is a front plan view of the head massager in accordance with the present invention for showing the front massage gasbag.
Figure 15:
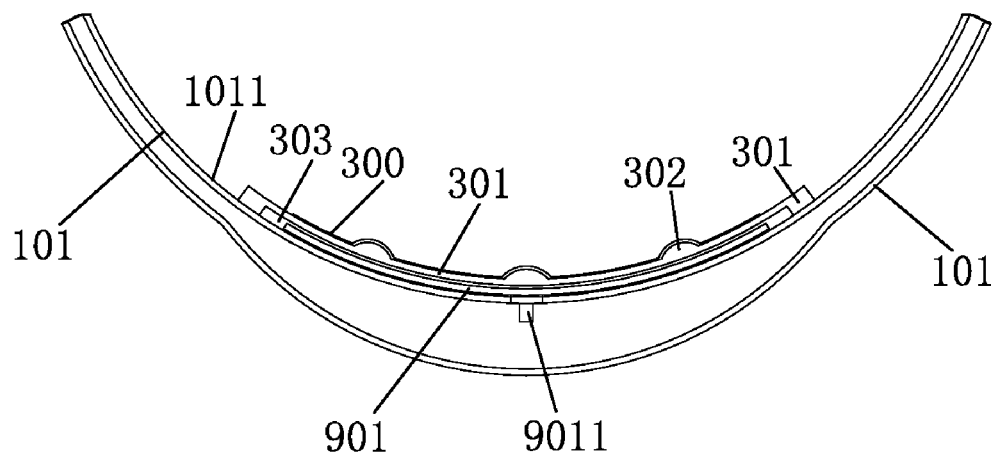
FIG. 15 is a diagram of the head massager in accordance with the present invention for showing a first massage pad, a first massage gasbag and a heater.
Figure 16:
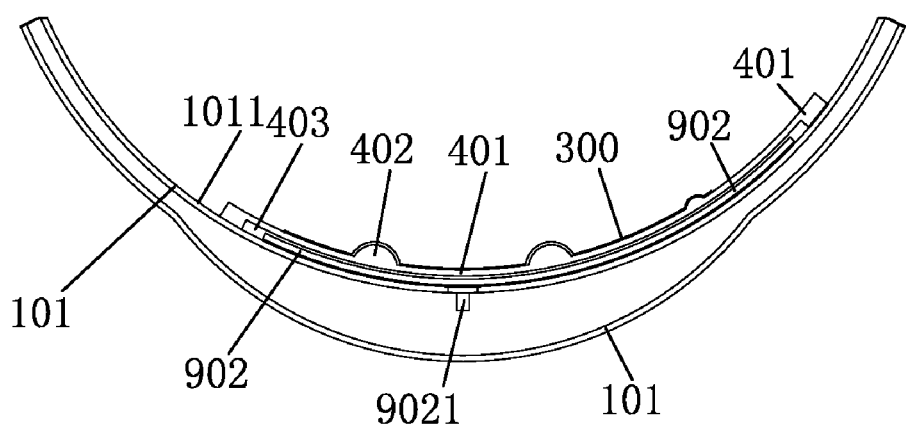
FIG. 16 is a diagram of the head massager in accordance with the present invention for showing a second massage pad, a second massage gasbag and the heater.
Figure 17:
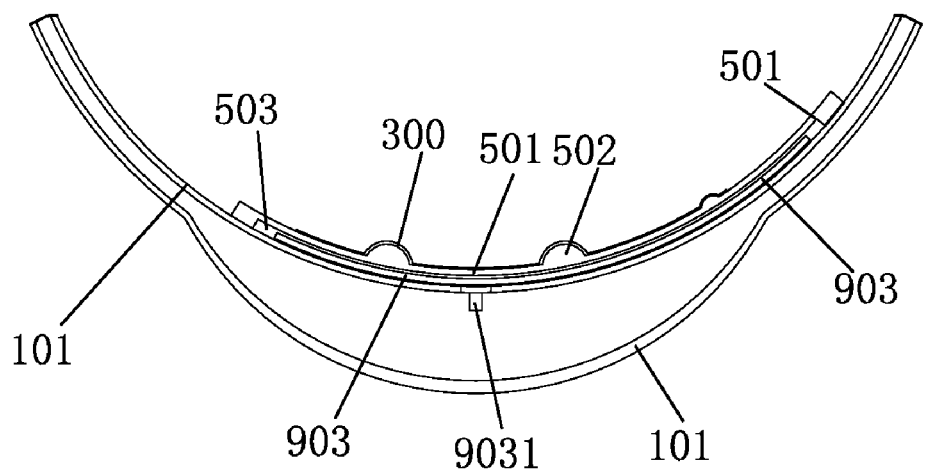
FIG. 17 is a diagram of the head massager in accordance with the present invention for showing a third massage pad, a third massage gasbag and the heater.
Figure 18:
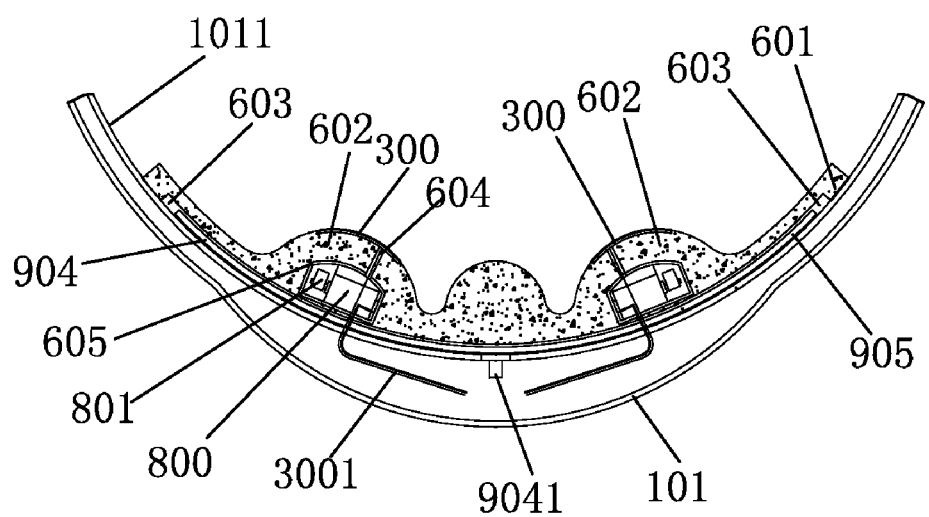
FIG. 18 is a diagram of the head massager in accordance with the present invention for showing a fourth massage pad, a fourth massage gasbag and the heater.
Figure 19:
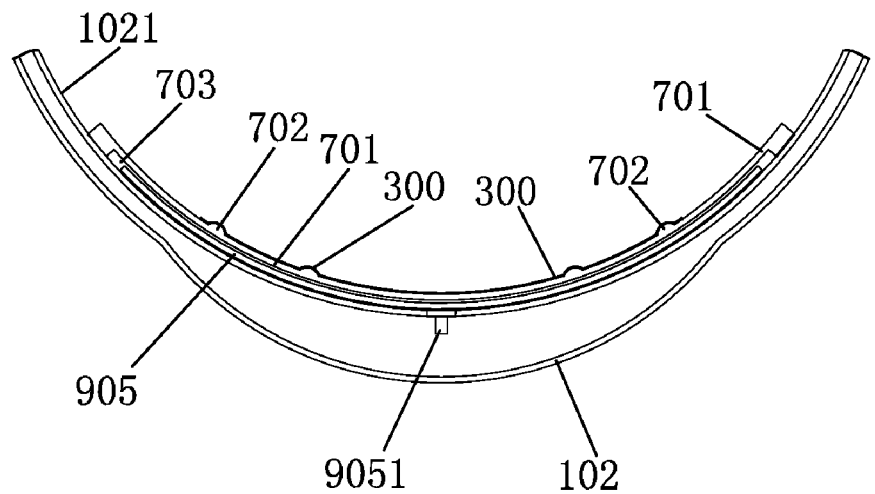
FIG. 19 is a diagram of the head massager in accordance with the present invention for showing a fifth massage pad, a fifth massage gasbag and the heater.
Figure 20:
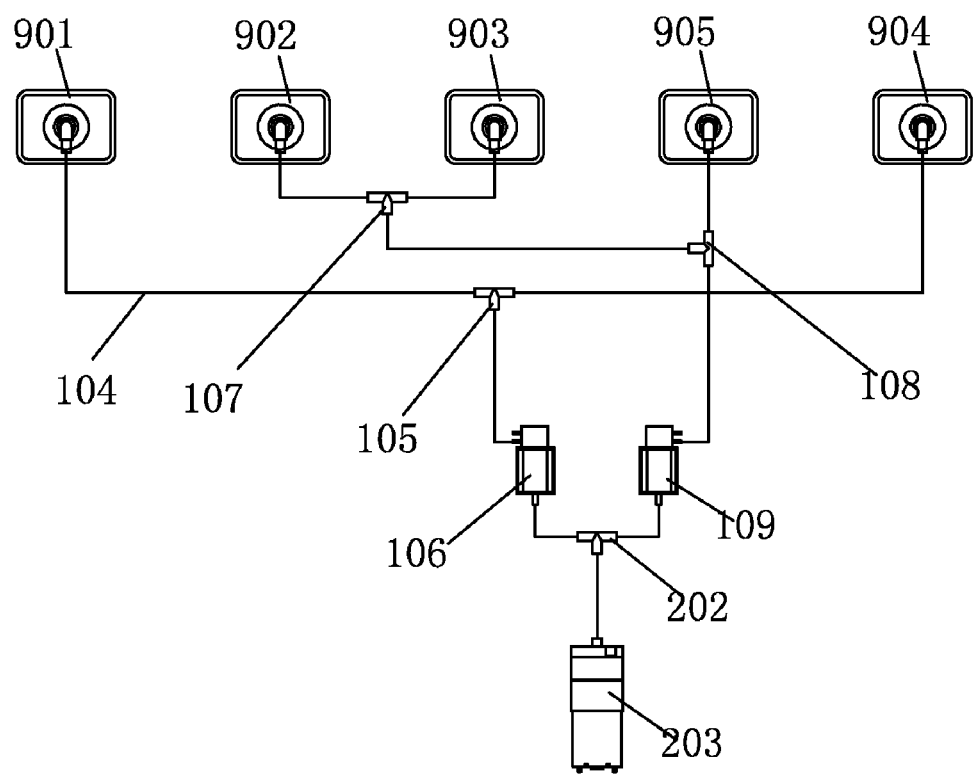
FIG. 20 is a diagram of the head massager in accordance with the present invention for showing a gas passage control way.
Figure 21:
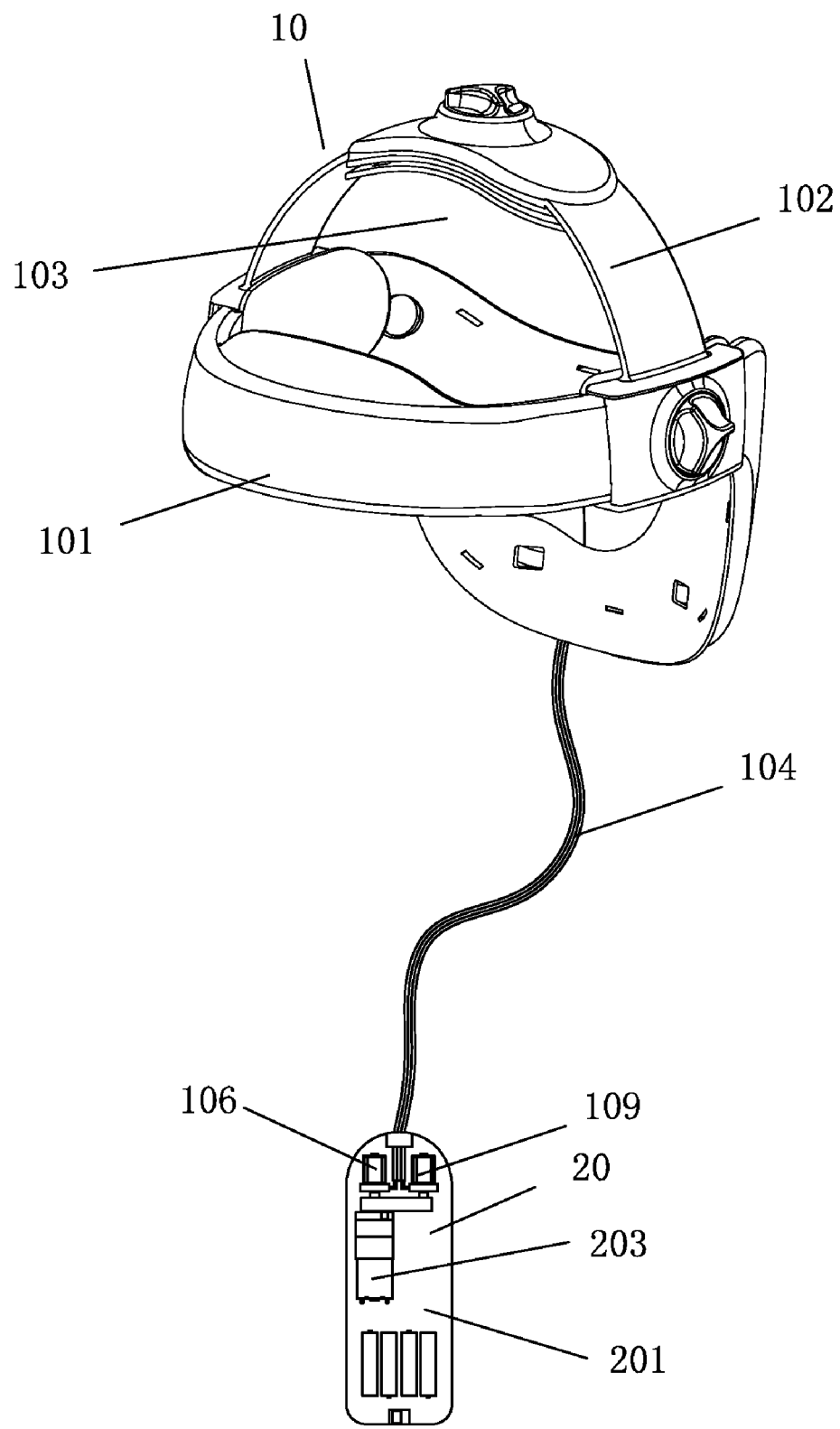
FIG. 21 is a perspective view of the head massager in accordance with the present invention.
Figure 22:
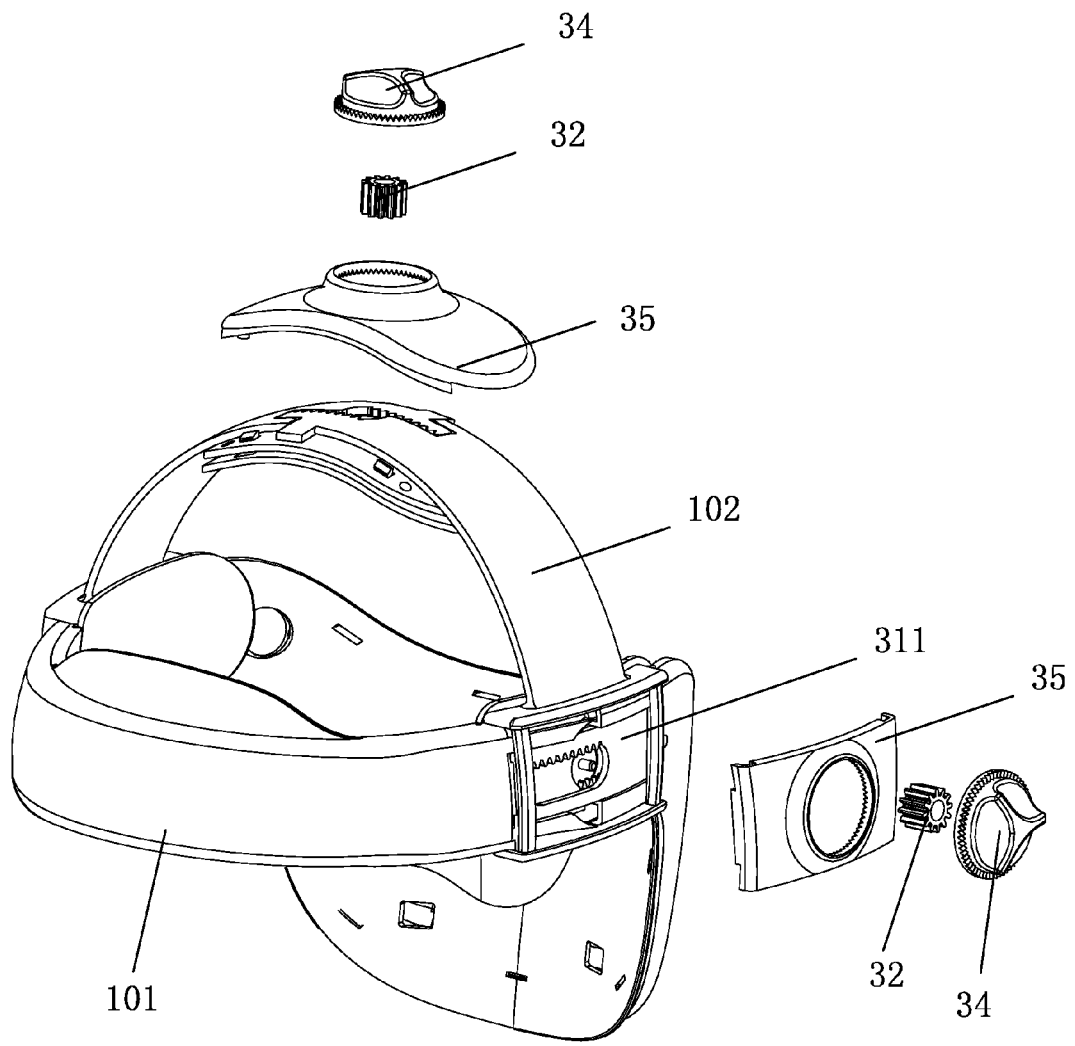
FIG. 22 is a partially exploded perspective view of the head massager in accordance with the present invention.
Figure 23:
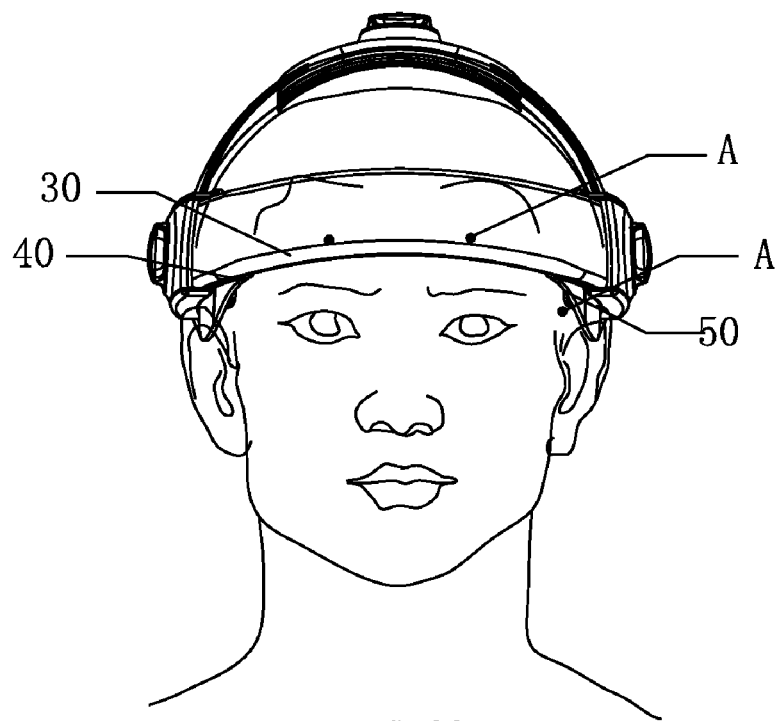
FIG. 23 is a front schematic view of the head massager in accordance with the present invention.
Figure 24:
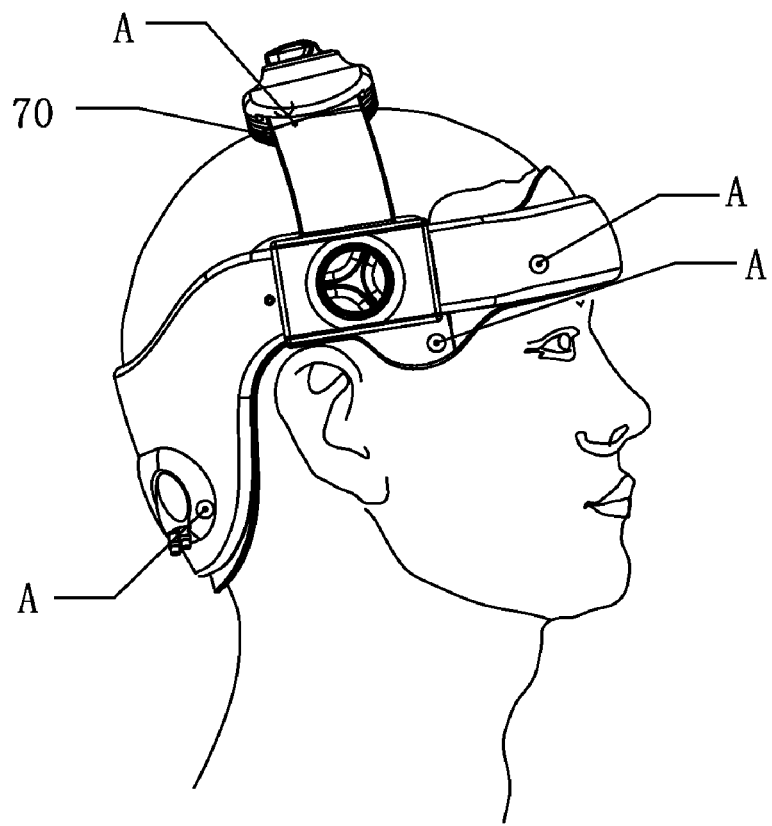
FIG. 24 is a side schematic view of the head massager in accordance with the present invention.
Figure 25:
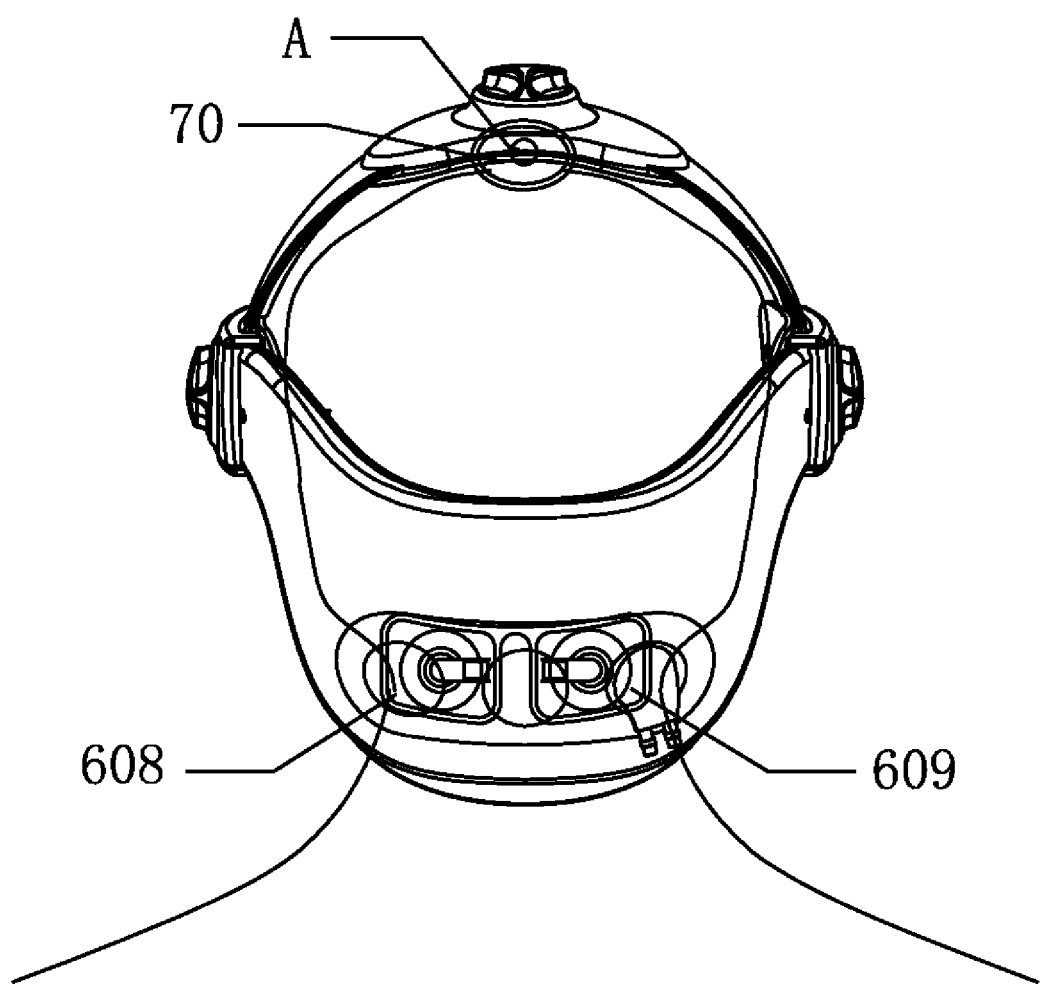
FIG. 25 is a rear schematic view of the head massager in accordance with the present invention.

With reference to FIGS. 11 to 25, the head massager in accordance with the present invention includes a helmet (10) and a control device (20). The helmet (10) has a parallel hoop (101) and an arc meridian hoop (102) diametrically mounted to the parallel hoop (101) to define a receiving space (103) for partially receiving user's head (80). The parallel hoop (101) has an inner periphery (101) facing the head (80) and a first massage pad (30), a second massage pad (40), a third massage pad (50) and a fourth massage pad (60) are respectively mounted on the inner periphery (1011) of the parallel hoop (101). The arc meridian hoop (102) has an inner periphery (1021) facing the head (80) and a fifth massage pad (70) is mounted on the inner periphery (1021) of the arc meridian hoop (102). Each of the massage pads (30, 40, 50, 60, 70) corresponds to an acupuncture point (A) on human head.

Each of the massage pads (30, 40, 50, 60, 70) has a base (301, 401, 501, 601, 701) with a pellet (302, 402, 502, 602, 702) raised thereon. The bases (301, 401, 501, 601, 701) and the pellets (302, 402, 502, 602, 702) are made of silica gel such that the bases (301, 401, 501, 601, 701) and the pellets (302, 402, 502, 602, 702) are elastic. The bases (301, 401, 501, 601, 701) are respectively adhered to the inner periphery of a corresponding one of the parallel hoop (101) and the arc meridian hoop (102). In addition, the pellets (302, 402, 502, 602, 702) can be respectively and integrally formed with the bases (301, 401, 501, 601, 701). A chamber (303, 403, 503, 603, 703) is defined between each of the bases (301, 401. 501, 601, 701) and the corresponding hoops (101, 102) for receiving a massage gasbag (901, 902, 903, 904, 905). Each massage gasbag is flat and has a nozzle extending into a corresponding one of the chambers that receiving the massage gasbag. Each of the massage pellets (302, 402, 502, 602, 702) has a heater (300) disposed thereon. The heater is received in a corresponding one of the pellets or directly adhered on the corresponding pellet. The control device (20) has a control box (21) for receiving a circuit board that has the control circuits formed thereon. In the preferred embodiment of the present invention, each massage pad has a recess defined therein for forming the chamber with the corresponding hoops.

The massage pellets (302, 402, 502, 702) of the massage pads (30, 40, 50, 70) has different height from one another. The fourth massage pad (60) has two massage gasbags (608, 609) disposed thereon and a trough (605) defined therein for receiving a vibrator (800). The vibrator (800) has a vibrating block (801) eccentrically mounted on a drive axle thereof such that the massage pellets is vibrated for massaging when the vibrator is operated. In addition, the fourth massage pad (60) has a groove (604) defined therein for a wire (3001) of the heater (300) and the wire of the wire of the vibrator (800) passing through the fourth massage pad (60) and connected to the circuit board in the control box (201).

The first massage gasbag (901) and the fourth massage gasbag (904) respectively has a nozzle (9011, 9041) connected to two ports of a first T-shaped air connector (105) via an air tube (104), and the other port of the first T-shaped air connector (105) is connected to a first electric valve (106) via an air tube. The second massage pad (902) and the third massage pad (903) respectively has a nozzle (9021, 9031) connected to two ports of a second T-shaped air connector (107). The other port of the second T-shaped air connector (107) and a nozzle (9051) of the fifth massage pad (905) are respectively connected to two ports of a third T-shaped air connector (108), and the other port of the third T-shaped air connector (108) is connected to a second electric valve (109). The first electric valve (106), the second electric valve (109) and an air pump (200) are respectively connected to three ports of a fourth T-shaped air connector (202). The first electric valve (106), the second electric valve (109) and the air pump (203) are received in the control box (200) for reducing the total weight of the helmet (10) and the noise during operating.

The operate principle of the head massager in accordance with the present invention is followed. The massage gasbags are continually pumped and exhausted via controlling the air pump (203) and the two electric valves (106, 109). The massage pad is raised when the massage gasbag is pumped and returned to the original shape when the massage gasbag is exhausted for pressure massaging the acupuncture points on the user's head. The massage pellets can execute vibrating massaging for the acupuncture points on the user's head when the vibrator is operated. The massage pellets can execute heating massaging for the acupuncture points on the user's head when the heater is operated. In addition, the air pump, the vibrator and the heater can be mutually operated for a multi-functional massage to user's head.

Although the invention has been explained in relation to its preferred embodiment, it is to be understood that many other possible modifications and variations can be made without departing from the spirit and scope of the invention as hereinafter claimed.

The invention claimed is:

1. A head massager, comprising:
  a first arc member comprising two first channels at both ends respectively and a series of first teeth formed on a lower edge of each of the first channels;
  a second arc member comprising two second channels at both ends respectively and a series of second teeth formed on an upper edge of each of the second channels;
  a first curved member comprising a series of third teeth formed on one end;
  a second curved member comprising a series of fourth teeth formed on one end;
  first, second, and third seats each comprising a stub extending outwardly wherein (a) the first seat is formed at the other end of the first curved member, the first channel at one end of the first arc member is disposed in the first seat, the second channel at one end of the second arc member is disposed in the first seat, the second channel at one end of the second arc member is partially placed over the first channel at one end of the second arc member, and the stub of the first seat passes both the first channel at one end of the first arc member and the second channel at one end of the second arc member; (b) the second seat is formed at the other end of the second curved member, the first channel at the other end of the first arc member is disposed in the second seat, the second channel at the other end of the second arc member is disposed in the second seat, the second channel at the other end of the second arc member is partially placed over the first channel at the other end of the second arc member, and the stub of the second seat passes both the first channel at the other end of the first arc member and the second channel at the other end of the second arc member; and (c) the stub of the third seat is disposed between the third teeth and the fourth teeth; and
  first, second, and third distance adjustment devices each comprising an elastic member put on the stub of one of the first, second, and third seats, a drive gear put on the elastic member such that the elastic member is positioned between the stub of the seat and the drive gear, a sliding knob urged by the elastic member and including outer annular teeth and inner annular teeth meshing with the drive gear, and a cover including an opening and inner annular teeth formed on the opening, the cover being releasably secured to one of the first, second, and third seats to have the inner annular teeth meshing with the outer annular teeth of the sliding knob in a locked position;
  wherein the drive gear of the first distance adjustment device is meshed with both the first teeth at one end of the first arc member and the second teeth at one end of the second arc member;
  wherein the drive gear of the second distance adjustment device is meshed with both the first teeth at the other end of the first arc member and the second teeth at the other end of the second arc member;
  wherein the drive gear of the third distance adjustment device is meshed with both the third teeth and the fourth teeth; and
  wherein the sliding knob of each of the first, second, and third distance adjustment devices is manually movable to cause the outer annular teeth thereof to disengage from the inner annular teeth of the corresponding cover of each of the first, second, and third distance adjustment devices so that a subsequent pivotal movement of the sliding knob of each of the first, second, and third distance adjustment devices rotates the meshed drive gear.

* * * * *